(12) United States Patent
Beaudoin et al.

(10) Patent No.: US 10,794,796 B2
(45) Date of Patent: Oct. 6, 2020

(54) ENGINEERED DETECTION SWAB

(71) Applicant: PURDUE RESEARCH FOUNDATION, West Lafayette, IN (US)

(72) Inventors: Stephen P Beaudoin, West Lafayette, IN (US); Bryan William Boudouris, Lafayette, IN (US); Michelle Chaffee-Cipich, Greenwood, IN (US); Aaron James Harrison, Aurora, UT (US); Stefan Lukow, Washington, DC (US); Lizbeth Rostro, Lake Jackson, TX (US); Caitlin Joy Schram, Troy, MI (US); Kathryn Maureen Smith, West Lafayette, IN (US); Myles Calvin Thomas, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 705 days.

(21) Appl. No.: 14/858,768

(22) Filed: Sep. 18, 2015

(65) Prior Publication Data
US 2016/0084740 A1 Mar. 24, 2016

Related U.S. Application Data

(60) Provisional application No. 62/052,375, filed on Sep. 18, 2014.

(51) Int. Cl.
*G01N 1/02* (2006.01)
*G01N 33/22* (2006.01)
*C08G 61/12* (2006.01)
*C08K 7/02* (2006.01)

(52) U.S. Cl.
CPC .............. *G01N 1/02* (2013.01); *C08G 61/126* (2013.01); *G01N 33/227* (2013.01); *C08G 2261/1412* (2013.01); *C08G 2261/3223* (2013.01); *C08G 2261/512* (2013.01); *C08G 2261/592* (2013.01); *C08G 2261/93* (2013.01); *C08G 2261/94* (2013.01); *C08K 7/02* (2013.01); *G01N 2001/022* (2013.01); *G01N 2001/028* (2013.01)

(58) Field of Classification Search
CPC ...... C08K 7/02; G01N 1/02; C01N 2001/028; C01N 2001/022; C01N 1/02; H01G 11/48; H01G 9/2068; C08G 2261/94; C11D 17/049; C11D 17/044
USPC ........................................ 15/209.1; 428/292.1
See application file for complete search history.

(56) References Cited

U.S. PATENT DOCUMENTS 5,858,537 A * 1/1999 Brown ................ H01L 23/3732
156/167
2010/0318193 A1* 12/2010 Desai ...................... A61L 27/04
623/23.76

OTHER PUBLICATIONS

Polythiophene, wikipedia, accessed online Jan. 7, 2018.*

* cited by examiner

*Primary Examiner* — Camie S Thompson
(74) *Attorney, Agent, or Firm* — Purdue Research Foundation

(57) ABSTRACT

A novel, advanced polymeric swab is disclosed herein. The swabs have a surface texture that allows for independent motion between microscale regions, are reusable with no loss of accuracy or efficiency, and are fabricated from optoelectronically-active elements to minimize static charging during repeated use.

13 Claims, 15 Drawing Sheets

ENGINEERED DETECTION SWAB

CROSS-REFERENCE TO RELATED APPLICATIONS

The present U.S. patent application is related to and claims the priority benefit of U.S. Provisional Patent Application Ser. No. 62/052,375, filed Sep. 18, 2014, the contents of which is hereby incorporated by reference in its entirety into this disclosure.

STATEMENT OF GOVERNMENT INTEREST

This invention was made with government support under 2010-ST-108-LR0003 and 2013-ST-061-ED0001 awarded by the U.S. Department of Homeland Security, Science and Technology Directorate. The government has certain rights in the invention.

TECHNICAL FIELD

The present disclosure generally relates to inspection devices for inspecting for explosive materials and other materials, and in particular to a swab-based inspection scheme.

BACKGROUND

This section introduces aspects that may help facilitate a better understanding of the disclosure. Accordingly, these statements are to be read in this light and are not to be understood as admissions about what is or is not prior art.

Contact-based swabbing is an invaluable element in the overall trace explosives detection toolbox that is applied for improving the security of persons, transport, cargo, and infrastructure.

However, current swab technology for contact-based sampling is not optimized to interrogate the surfaces being sampled. In particular, experimental and modeling work conducted to date suggests that a swab with better-engineered surface characteristics will provide superior performance to that currently achieved. Therefore, there exists a need to develop novel materials with nano-/micro-structured active layers in order to improve the collection efficiency of the swabs.

SUMMARY

In one aspect, a polymeric swab is disclosed. The polymeric swab has a plurality of microfabricated fibers. The plurality of microfabricated fibers are configured to contain a surface texture that allows for independent motion between microscale regions. In another aspect, the plurality of microfabricated fibers are optimally configured to interrogate surfaces. In yet another aspect, the plurality of microfabricated fibers have characteristic heights and diameters. In another aspect, the plurality of microfabricated fibers are reusable.

In another aspect, the plurality of microfabricated fibers are fabricated from optoelectronically-active elements to minimize static charging during repeated use. In yet another aspect, the plurality of microfabricated fibers are thermally stable. In yet another aspect, the plurality of microfabricated fibers are polythiopene based polymers. In yet another aspect, the polymer swab also has polymers configured to not outgas at ion-mobility spectrometry conditions.

In yet another aspect, a process for assembling a polymeric swab is disclosed. The process includes the steps of producing a mold on a substrate from an anodized aluminum oxide template with pores that span a range of prescribed nominal diameters, containing a specified thickness, impregnating a polymer in the melt state into the pores of the mold, electrodepositing nanorods in the pores, lowering the temperature to below crystallization transition temperature, and removing the template.

DETAILED DESCRIPTION

Figure 1:
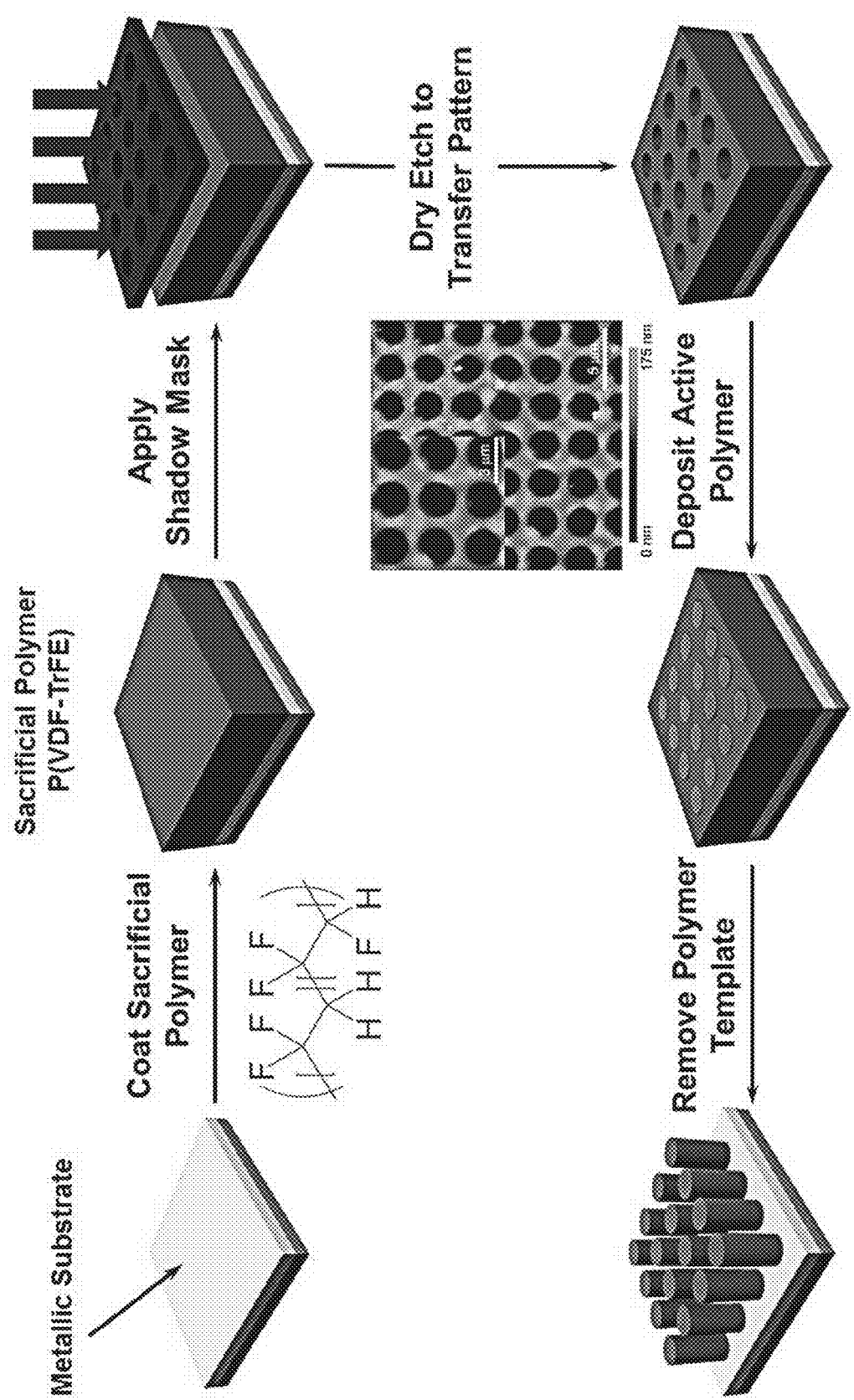
FIG. 1 is a schematic illustration of one embodiment of fabricating the swabs.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel, advanced polymeric swab is disclosed herein. These swabs have a surface texture that allows for independent motion between microscale regions with characteristic heights and diameters ranging from approximately 1-25 μm, are reusable with no loss of accuracy or efficiency, are fabricated from optoelectronically-active elements to minimize static charging during repeated use, and are thermally stable at temperatures between 250° C. and 350° C.

In one embodiment, the swabs are fabricated by growing into or patterned using templates from sacrificial polymer masks. Referring to FIG. 1, which is a schematic illustration of one embodiment of fabricating the swabs, the swabs are fabricated by first patterning a sacrificial polymer (preferably one with high thermal and chemical resistance, for example, poly(vinylidenefluoride-co-trifluoroethylene) (P(VDV-TrFE)) through a shadow match using a dry etching technique. Still referring to FIG. 1, the inset atomic force microscopy (AFM) image evidences this technique can be accomplished on the microscale. An electrically-conductive polymer is then deposited in the pores of the material, and the template is removed selectively, thereby resulting in a freestanding film of micropatterned polymer wires. It should be noted that in FIG. 1, the featured texturing on the swab surface appears uniform for the purposes of simplicity in creating the schematic and is not to be indicative of the actual swabs. The swabs may have surface textures that vary dramatically at the micro-scale and nano-scale over the entire width of the swab.

It should also be noted the herein disclosed swabs may be designed for applications in existing sampling swabs or as virtual drop-in replacements for existing swabs. Due to the texturing of the herein disclosed swabs, and their high thermal and mechanical stability, and their resistance to charging, they offer superior performance over the existing swabs. These swab characteristics are delivered using polymeric films manufactured via electropolymerization into inexpensive, commercially-available polymer templates patterned using commercially-available masks. In addition, the key aspect of the herein disclosed fibers is their ability to move independently from one another and to deform to penetrate into features on the surface being sampled. The fibers also maintain their mechanical strength during use (including maintaining size, shape, elastic properties, and stiffness), harvest the residue effectively and release it in the detector, and not degrade chemically when cycled repeatedly through the process of sampling/detection. Also, the fibers and base polymer do not necessarily need to be made from the same material; rather, there can be chemical differences between the fiber and base polymer. The fibers can also be attached to a handle-like device using an adhesive, by chemical bonding, by melting one or more materials to cause them to adhere, or by pressing them together. Moreover, the fibers may have varying heights and diameters, and thus need not be uniform. Regarding spacing between each brush and fiber, a topography of brush fibers that covers the range of likely topographical features and residue sizes on the surface to be sampled is a key factor in determining optimal spacing. These range from 10-100 nm to 100's of microns. Most key features are between 10 and a few hundred microns.

Figure 2A:
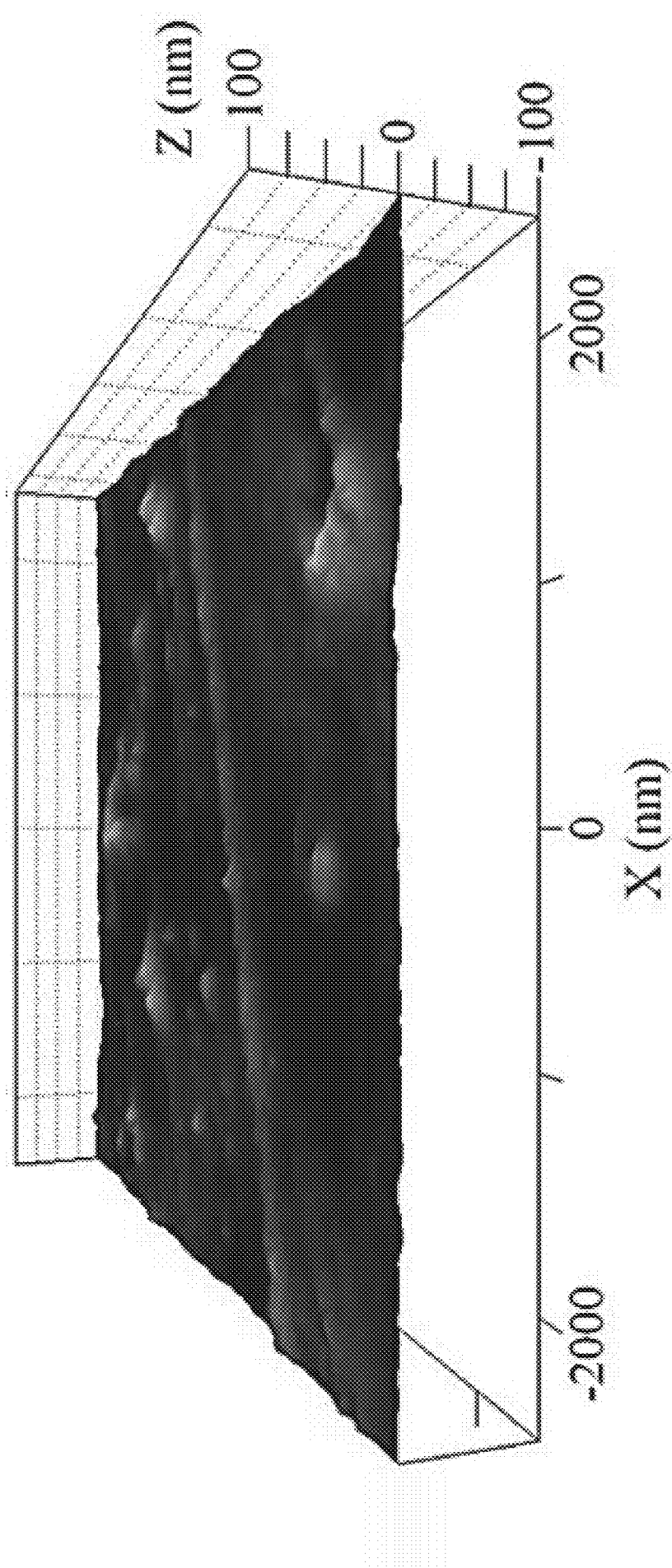
FIG. 2a shows the atomic force microscopy (AFM) surface topographical scan of a 5 μm×5 μm region on acrylic melamine (clear coating).
Figure 2B:
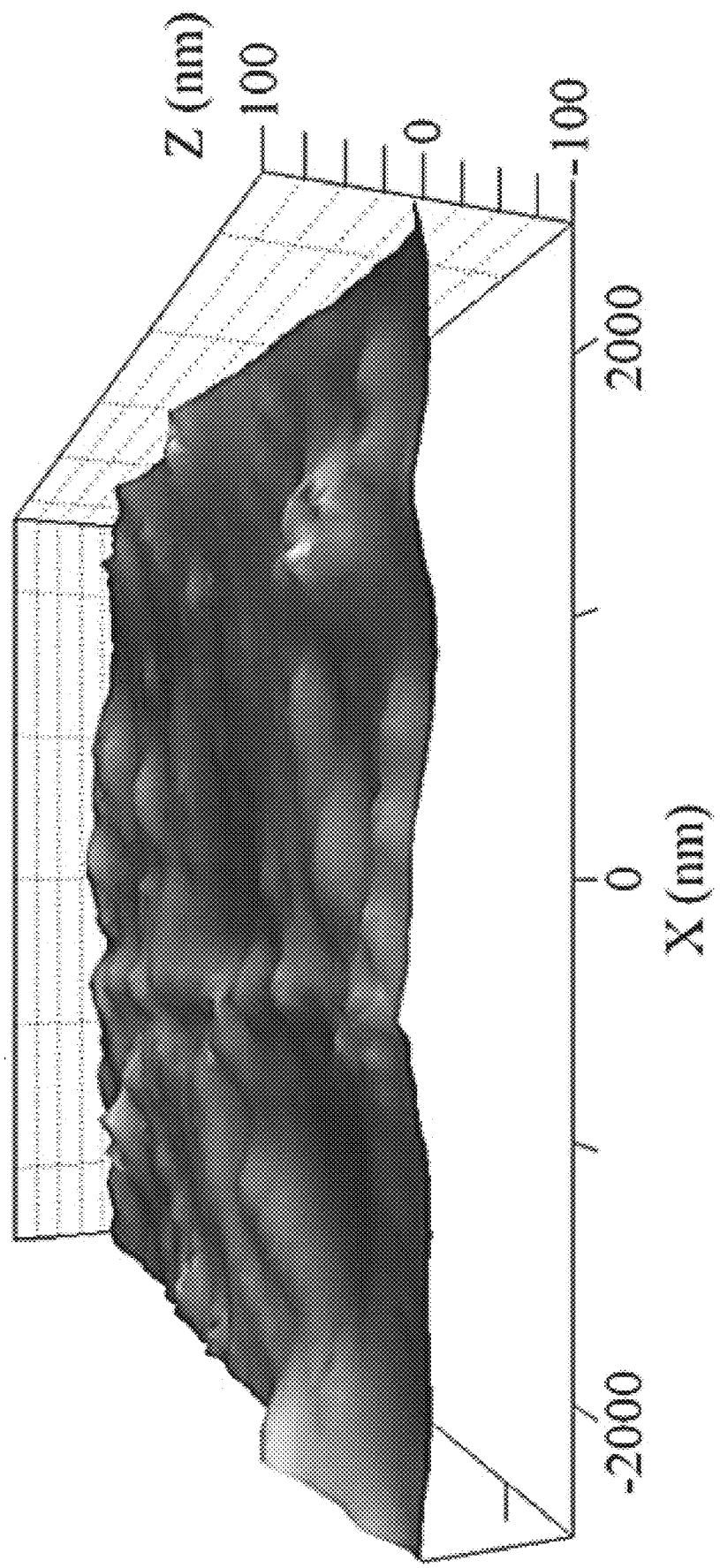
FIG. 2b shows the AFM surface topographical scan of a 5 μm×5 μm region on polyester acrylic melamine (white coating).
Figure 2C:
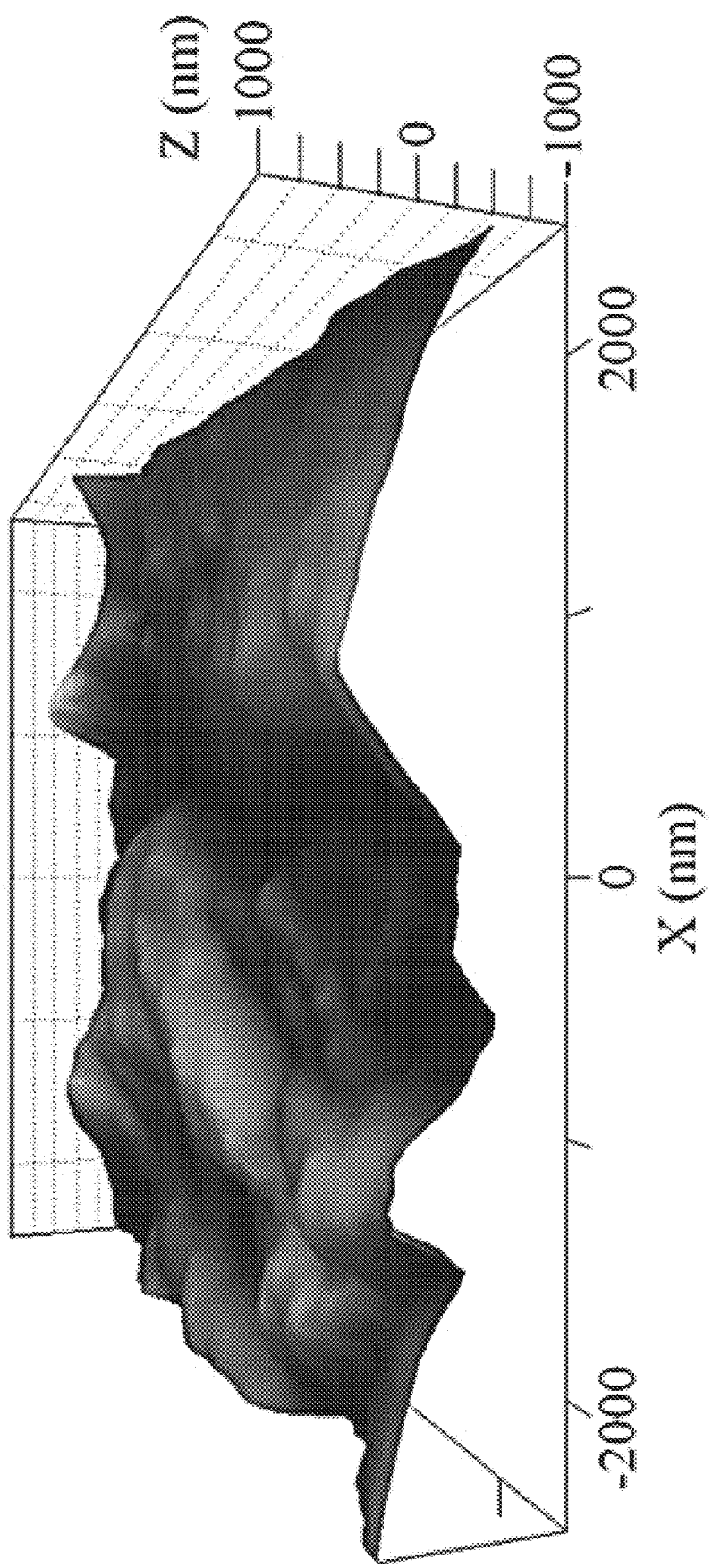
FIG. 2c shows the AFM surface topographical scan of a 5 μm×5 μm region on green anti-reflective military finish.

In one embodiment, interrogation of surface topography to remove residues embedded beneath the top of the substrate surface is performed. This interrogation involves quantifying both the space on the substrate in which a residue may be and the elements of the swab that may interrogate these regions to remove residue. It also allows evaluation of the effectiveness of the swabs at deforming to enter these regions and the likelihood that substrates could be damaged through the swabbing process. Referring to FIGS. 2a-2c, exemplary topographical scans of aluminum substrates with three different coatings are shown. The scans were generated by atomic force microscopy (AFM) and converting the raw data into three-dimensional maps of the surfaces of substrates of interest. FIG. 2a shows the AFM surface topographical scan of a 5 μm×5 μm region on acrylic melamine (clear coating), FIG. 2b shows the AFM surface topographical scan of a 5 μm×5 μm region on polyester acrylic melamine (white coating), and FIG. 2c shows the AFM surface topographical scan of a 5 μm×5 μm region on green anti-reflective military finish. The topographies of the properties of the substrates and swabs as shown in FIGS. 2a-2c were articulated using a Fourier-transform approach to develop a nanoscale model of the substrate topography. Such a simulation allows different residue contact challenges during the sampling to be identified in silico. It should be appreciated that although only three different substrates are reported, other substrates are possible. As examples, these other substrates may be rough plastic, smooth plastic, vinyl luggage handle, cardboard, plywood, nylon fabric (for example, gym/duffel bags), glass (for example, a cell phone screen), and leather (for example, a belt). Similarly, for each of these substrates, a fast Fourier transform (FTT) map of the surface may be generated to allow reproduction of the measured topography as well as simulation of the local topography at multiple different locations on the surface of the substrate.

Figure 3:
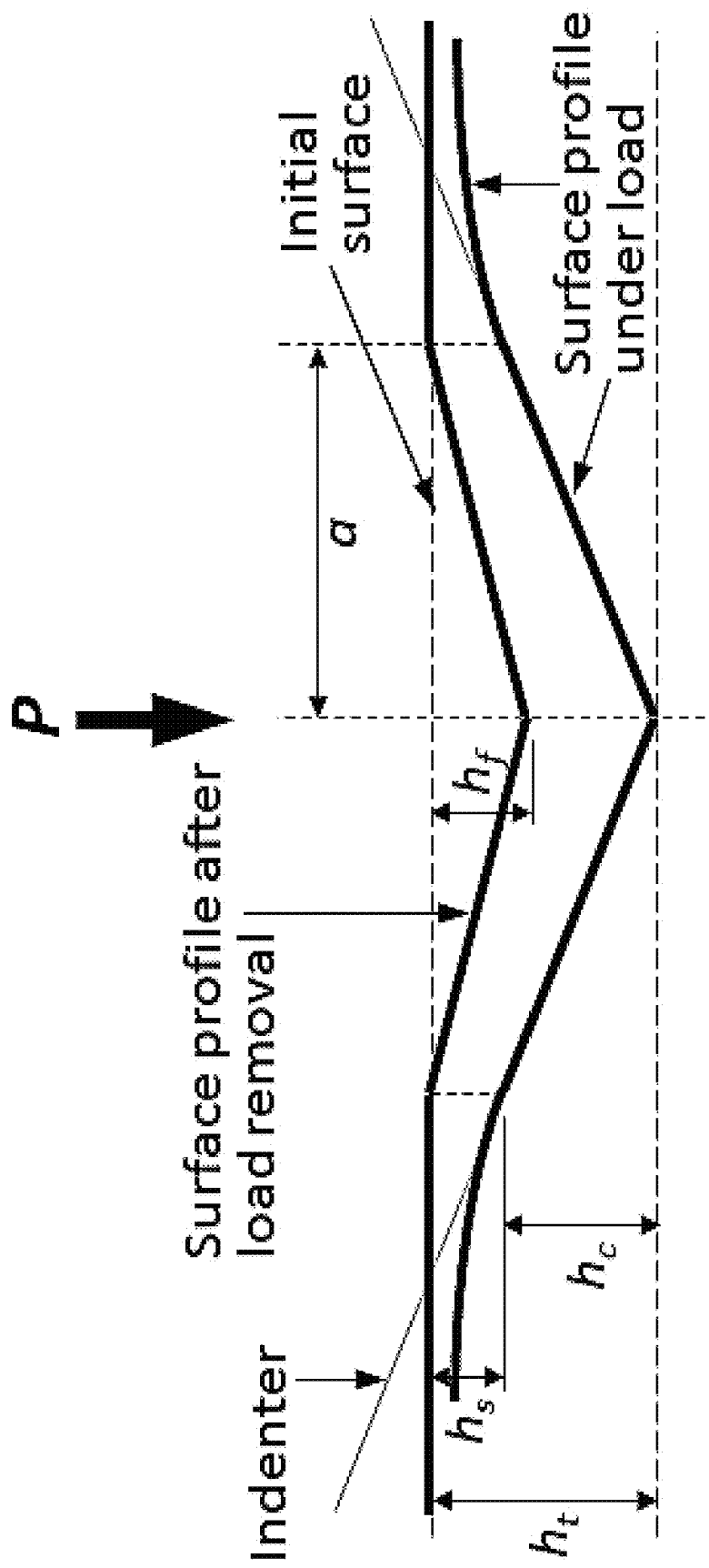
FIG. 3 is a schematic representation of deformation of a surface following application of a load from the corner of a cube.

In addition, characterization of adhesion and mechanical behavior of explosive compounds of interest under typical adhesive loads and swabbing stresses is performed (in this embodiment, explosives compounds are the compounds of interest). These adhesion forces are controlled by van der Waals interactions, hydrogen bonding, and (in certain high relative humidity environments) by capillary forces. The mechanical behavior of the residues includes deformation of the explosive composite under load, its deformation (in the case of plastic), and ultimate failure (it should be noted that adhesive failure will liberate some quantity of any given residue from the surface). For performing the characterization of the substrate and swab mechanical properties, nanoindentation is performed on the substrates and swabs using an AFM-based nanoindenter. These measurements define the forces that can be applied safely to the substrates during the swab-based interrogation process, as well as the expected deformation when a load is applied to the filaments/brushes/fibers on the swabs. Referring to FIG. 3, a schematic representation of deformation of a surface following application of a load from the corner of a cube is shown. If the substrates cannot withstand the forces applied by the swabs, the swabbing process will introduce surface damage on the substrates. Such an occurrence is not acceptable in many applications, and is a problem which the herein disclosed swabs seek to solve. Similarly, if the filaments/brushes/fibers on the swabs deform, it is possible they may be prevented from accessing subsurface regions on the substrates, and therefore detectable residue will risk being undetected due to the limitations of the now-deformed filaments/brushes/fibers. Two important related properties of the substrates and swabs are the Young's modulus and the hardness. Table 1 contains preliminary results of measured mechanical properties of selected substrates (namely, material finish, white finish, clear finish, cardboard, plastic (both rough and smooth), and vinyl).

TABLE 1

Measured Mechanical Properties of Substrates

| Material | Hardness (GPa) | Young's Modulus (GPa) |
|---|---|---|
| Military Finish | 0.19 ± 0.05 | 4.0 ± 0.8 |
| White Finish | 0.14 ± 0.02 | 2.3 ± 0.1 |
| Clear Finish | 0.14 ± 0.01 | 2.0 ± 0.1 |
| Cardboard | 0.09 ± 0.03 | 1.7 ± 0.2 |
| Plastic (Rough, Smooth) | 0.09 ± 0.03 | 1.6 ± 0.3 |

Figure 4:
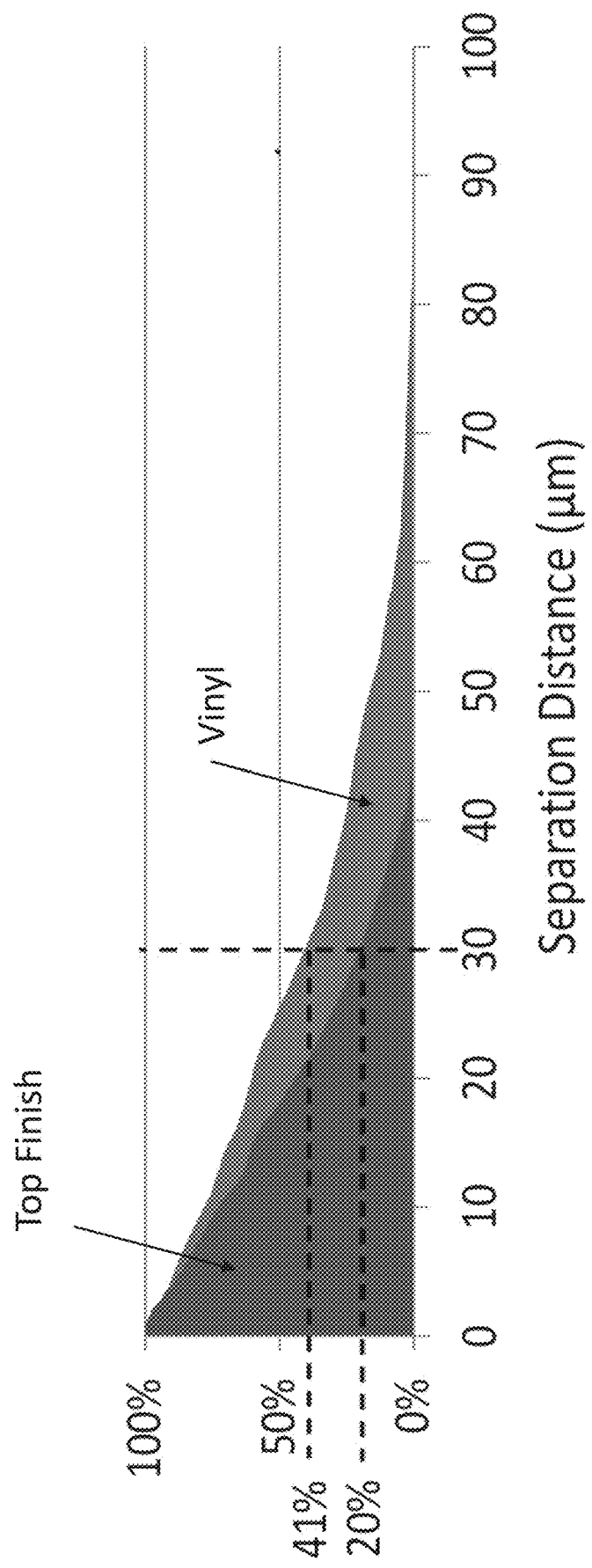
FIG. 4 is an example map showing predicted % of surface upon which a spherical explosive residue can avoid contact with a swab.

Combining the information from Table 1 with knowledge of the applied loads during swabbing allows prediction of the extent of deformation of the asperities on the substrate and swabs during swabbing, permitting further prediction of the fractional area of the substrate that can be interrogated by the swabs as a function of swab design and system operating conditions. FIG. 4 shows an exemplary example of such a result and is a map showing predicted % of surface upon which a spherical explosive residue can avoid contact with a swab. For purposes of FIG. 4, "top finish" represents aluminum with a clear coat finish. Still referring to FIG. 4, 20% of the surface area of an aluminum surface with a clear coat finish, and 41% of a vinyl luggage handle surface will allow spherical particles of explosive residue of 30 micron diameter to avoid detection by a swab. It should be appreciated that FIG. 4 represents only one embodiment of the present disclosure. Similar models may be generated for other substrates.

Explosives compounds and swabs adhere to solid surfaces due to three general classes of forces. These include van der Waals forces, hydrogen bonding, and capillary forces. At relative humidity (RH) levels less than about 55%, water will exist on surfaces as molecular water and will form hydrogen bonds between the surface and any adherent particles. At RH levels greater than 55%, the water will exist in continuum form, and will form liquid droplets between the interacting explosive and substrate. As examples, the following explosives compounds will be considered and described herein: ammonium nitrate/fuel oil (ANFO) Semtex 1A, and C4, in addition to trinitrotoluene (TNT). For the purpose of these examples, ANFO and TNT are used, but simulants of C4 and Semtex 1A are applied. Specifically, the simulants will contain all of the same matrix materials, but will contain particles of silica coated with energetic species rather than the actual energetic species. These particles are of comparable size to the energetic species particles in live compounds, but will not have enough energetic materials in the coatings to support detonation. Van der Waals forces between these materials and both: 1) the substrates from the first phase and 2) the swabs fabricated as disclosed herein, are measured indirectly via two different modes. As shown in Equation 1, the Hamaker constant (A), which is the fundamental constant in van der Waals force expressions, is obtainable as the relationship between each individual material (in Equation 1, the subscripts "1," "2," and "3" each denote Material 1, Material 2, and Material 3, respectively) interacting with itself across a vacuum.

$$A_{132} \approx (\sqrt{A_{11}} - \sqrt{A_{33}})(\sqrt{A_{22}} - \sqrt{A_{33}}) \quad (1)$$

AFM is used with a force scanner (for example, a PicoForce® (Bruker) scanner in contact mode)) to utilize Equation 1. Measurements are made under controlled relative humidity using an in-house humidity chamber to regulate the air surrounding the system to the desired RH±2%. To isolate van der Waals forces, an RH of 15% is desired. To eliminate electrostatic interference, an ionizer (for example, a StaticMaster® ionizer from Amstat Industries, Inc.) is introduced to the system. This ionizes the air in the vicinity of the probe, and the ions adsorb on the interacting surfaces to neutralize any charge on these surfaces and thus eliminate electrostatic effects. AFM probes (for example, Bruker® tipless MLCT AFM probes) may be used with a silica sphere attached to the end of the cantilever, to enable colloidal probe microscopy (CPM) measurements. With this approach, the adhesion between the silica probe and the explosives (simulant of C4, simulant of Semtex 1-A, ANFO, TNT) is measured directly, as is the adhesion between the silica and the substrates and the swabs. The topography of the silica sphere is measured using a second AFM cantilever, as is the topography of the explosives and the swab. This information (force, topography of interactive surfaces) is fed into a simulator which calculates the Hamaker constant ($A_{132}$ in Equation 1) from this information. In this example, Material 1 is silica, and its self-Hamaker constant (AR) is known. Air is the medium between the interacting surfaces (Material 3), and its self-Hamaker constant ($A_{33}$) is zero. The only remaining unknown in Equation 1 is $A_{22}$, which is the self-Hamaker constant for the explosive, the substrate, or the swab, depending on the system of interest. In this manner, Hamaker constants may be obtained for energetic material against the explosive binders of interest—which subsequently allows the analysis of each interaction in a swab-explosive-substrate composite.

A second approach for evaluating the Hamaker constant in the swab-explosive-substrate system involves the surface energy of the interacting materials. With this approach, one can relate the surface energy to the self-Hamaker constant by Equation 2.

$$A_{ii} \approx -2.1 * 10^{-21} \gamma \quad (2)$$

Figure 5A:
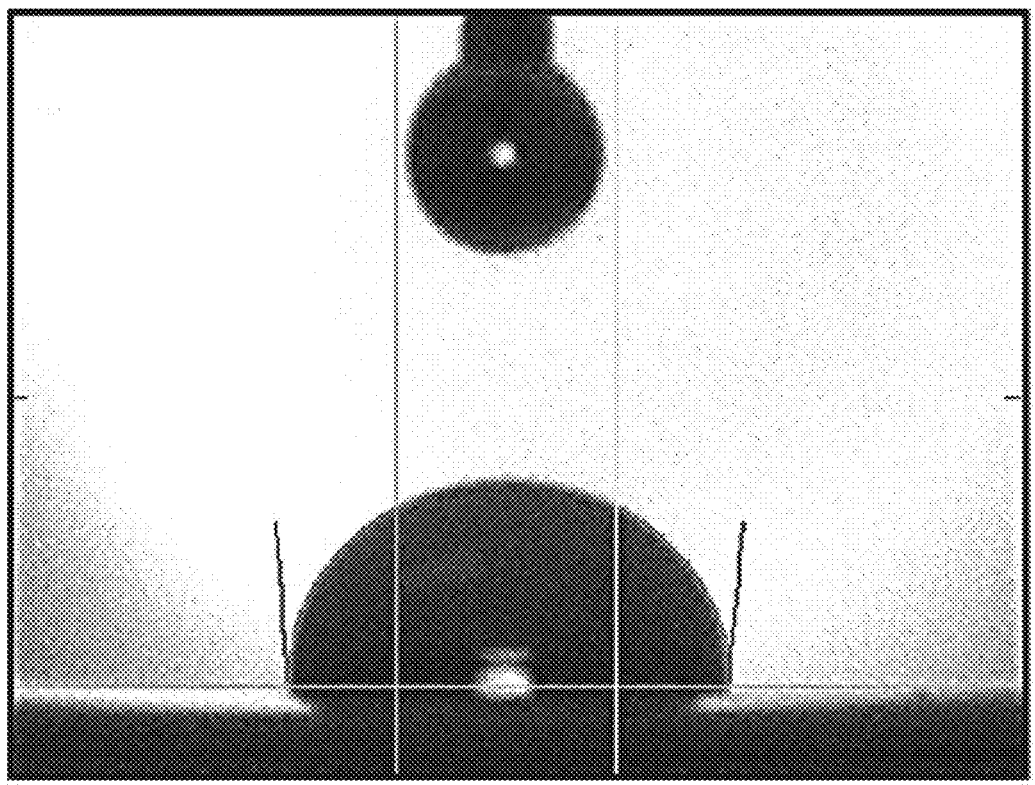
FIG. 5a is an image illustrating that the contact angle may be obtained through contact angle goniometry by measuring the angle of a drop of liquid placed on the surface.
Figure 5B:
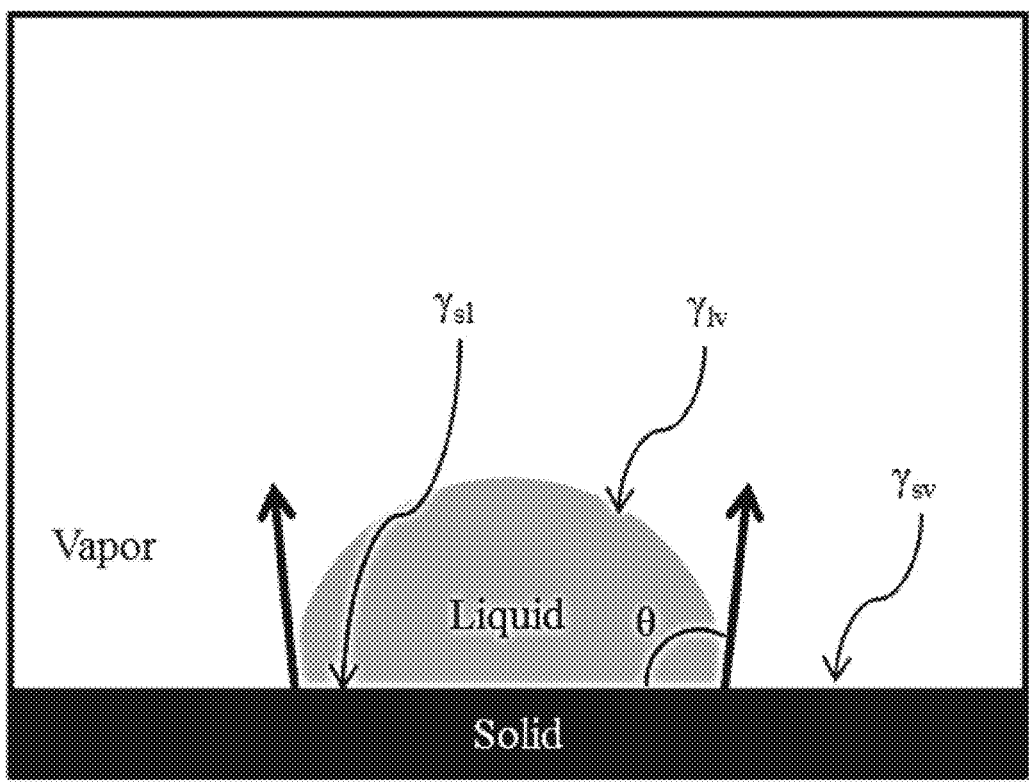
FIG. 5b an image similar to FIG. 5a illustrating that the contact angle may be obtained through contact angle goniometry by measuring the angle of a drop of liquid placed on the surface.

Now that the Hamaker constant calculation has been simplified, the surface energy, $\gamma$, must be obtained. The surface energy of a system is described by Equation 3 (Young's equation), $$\cos \theta \gamma_{lv} = \gamma_{sv} - \gamma_{si} - \pi_e \quad (3)$$

where subscripts s, l, and v represent the solid, liquid, and vapor species in the system, $\pi_e$ is the equilibrium pressure of the adsorbed vapor of the liquid on the solid (which can be assumed to be negligible), and $\theta$ is the measured contact angle of a liquid of interest on the solid. The contact angle ($\theta$) may be readily obtained through contact angle goniometry by measuring the angle of a drop of liquid that is placed on the surface, as shown in FIGS. 5a and 5b. A surface energy value can be broken into polar (hydrogen bonding, $\gamma^h$) and nonpolar (dispersive, $\gamma^d$) components. By manipulating Equation 3 and considering the polar and nonpolar components of surface energy, one can develop the following general expression for the surface energy of a solid $$\gamma_l \frac{(1+\cos\theta)}{2\sqrt{\gamma_l^d}} = \sqrt{\gamma_s^h}\left(\frac{\sqrt{\gamma_l^h}}{\sqrt{\gamma_l^d}}\right) + \sqrt{\gamma_s^d} \qquad (4)$$

where the polar and nonpolar components of the liquid surface energy, as well as the overall liquid surface energy, are known. When $$\left(\gamma_l \frac{(1+\cos\theta)}{2\sqrt{\gamma_l^d}}\right)$$

is plotted as a function of $$\left(\frac{\sqrt{\gamma_l^h}}{\sqrt{\gamma_l^d}}\right)$$

for a series of liquids on a given solid, the slope of the resulting straight line is $\sqrt{\gamma_s^h}$ and the y-intercept is $\sqrt{\gamma_s^d}$. These are the necessary quantities for the calculation of the solid surface energy ($\gamma$ in Equation 2).

Once the Hamaker constant is computed by the two methods outlined above and the surface roughness parameters are obtained, these are inputted to the simulator to obtain a predicted adhesion force distribution for swab-explosive or explosive-substrate interactions. These interactions can be compared across a number of material interactions to discover the "weak link" in a chain of materials. This weak link is the element in the stack comprised of the swab-residue-substrate where breakage will occur, leading to (desired) residue removal and detection.

After the van der Waals interactions between the swabs, explosives, and substrates have been determined, the effect of RH on the adhesion between these species may be assessed. Specifically, using the CPM method described above, measurements of the adhesion force between a well-characterized colloidal silica probe and the different solids may be performed in controlled RH environments ranging from 15-65% (it should be noted that the 15-65% only refers to a limitation that is due to the experimental equipment being used). The difference in adhesion between the CPM results at 15% RH and all other RH levels below 50% are attributed to adsorbed molecular water on one or both of the interacting surfaces.

Based on the topography and surface energy of the swabs, substrates, and explosives compounds, it is possible for nanodrops of continuum (bulk) moisture to exist on any or all of these surfaces at RH levels above ~50%. The Kelvin equation is used to predict the size of such droplets, as well as the force they exert to hold the residue onto the substrates or swabs. In the simplest case, where the contact angle of water against the two interacting surfaces is the same, the Kelvin equation is shown in Equation 5:

$$F_c = 2\pi r_p^2 \frac{RT\ln(RH)}{V_m} \qquad (5)$$

where $F_c$ is the capillary force between the interacting surfaces, $r_p$ is the wetted radius of contact between the liquid drop and asperities on one or the other of the interacting surfaces, R is the gas constant, T is the system temperature, RH is the relative humidity, and $V_m$ is the molar volume of water. While more complex forms of this equation are appropriate for a detailed analysis of capillary forces, such work is beyond the scope of this project. Rather, if RH effects are significant in the 50-65% RH range, Equation 5 provides a zeroth-order interpretation of the observed phenomenon. This is an appropriate to guide swab development.

Figure 6:
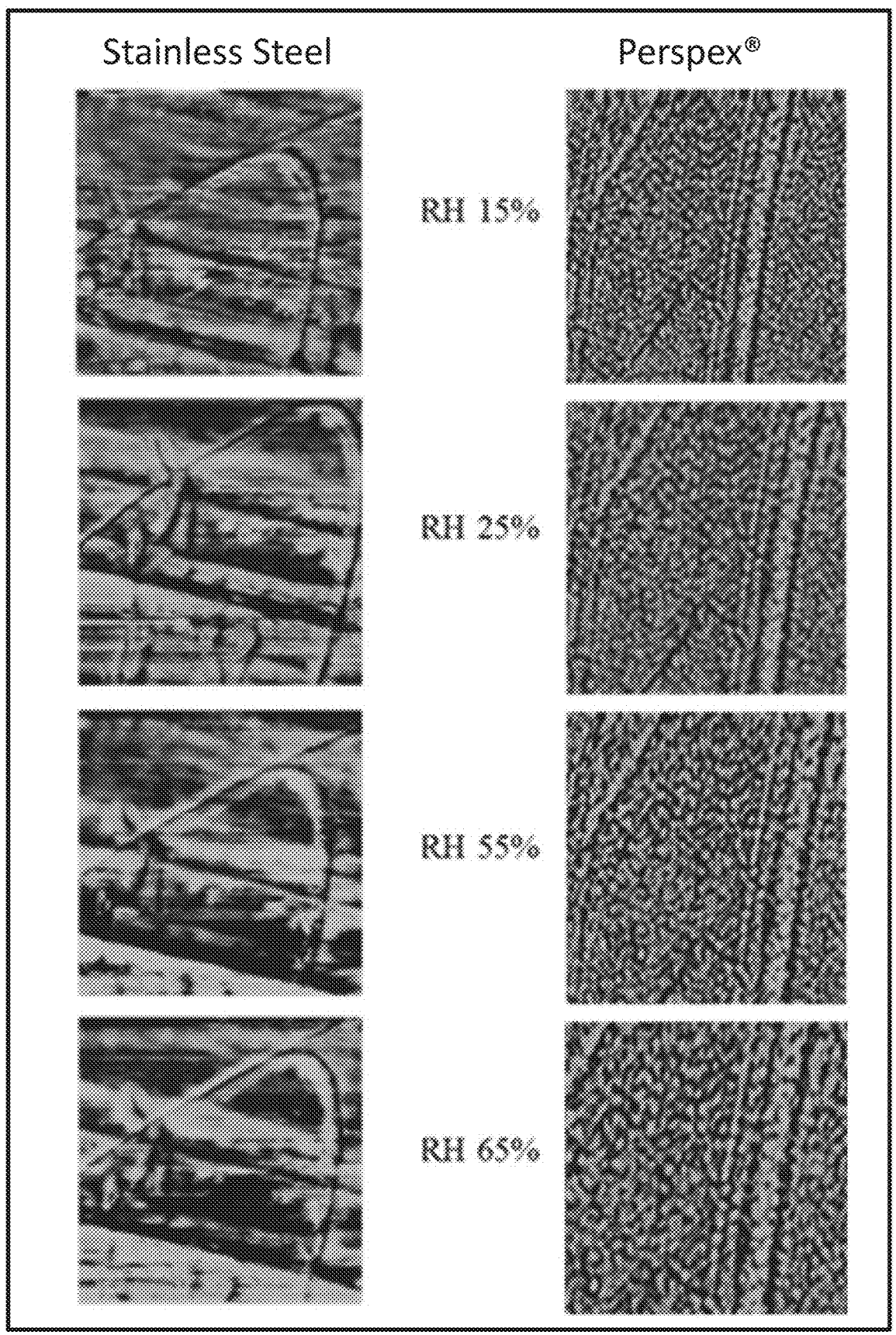
FIG. 6 shows phase contrast microscopy (PCM) images of the changing levels of adsorbed moisture on stainless steels and PERSPEX® at varying relative humidity (RH) levels.
Figure 7:
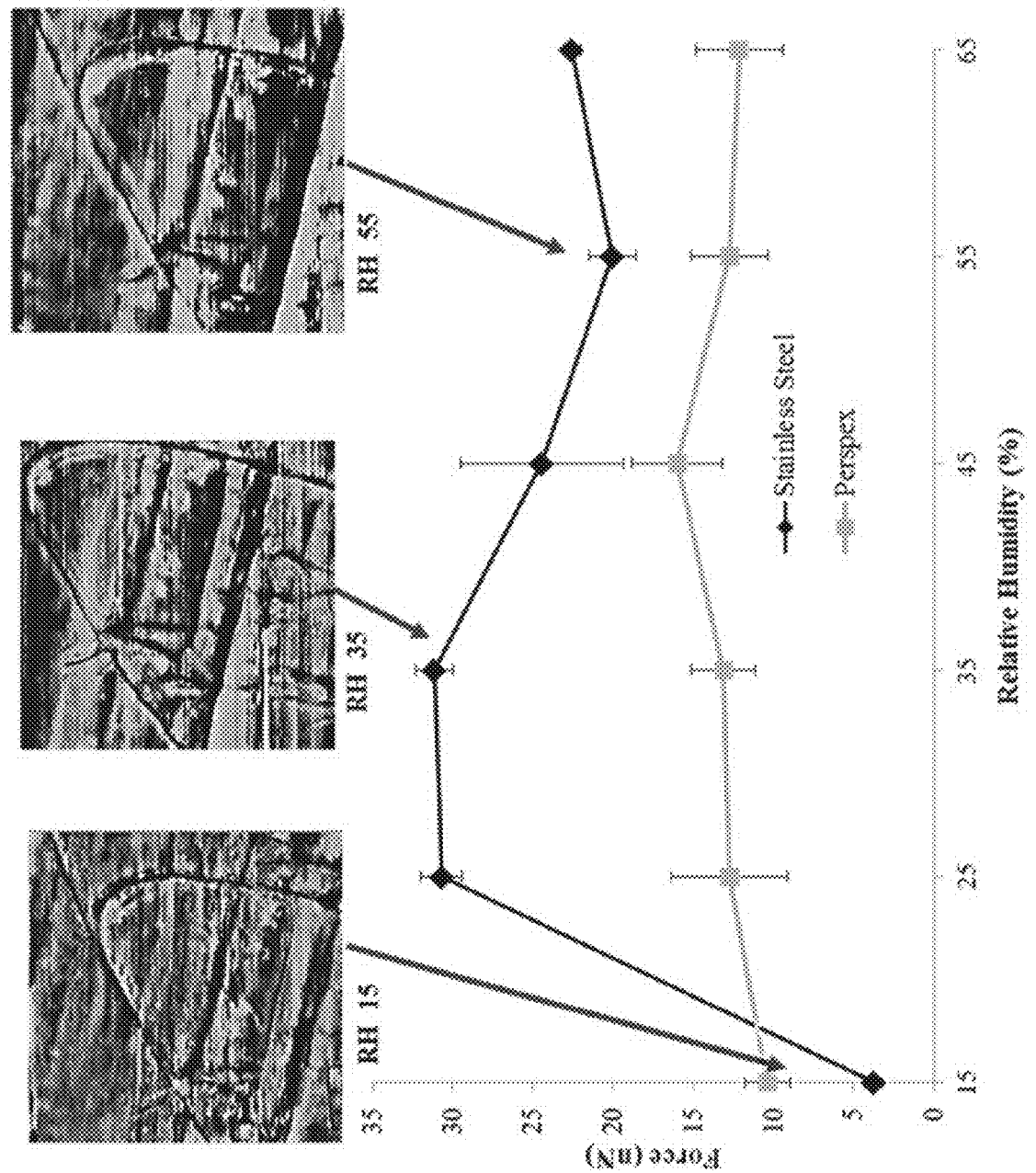
FIG. 7 is a plot showing measured adhesion forces between a silicon nitride cantilever probe and a stainless steel and a PERSPEX® substrate, with inlaid PCM portraits of stainless steel at varying RH.

Phase contrast microscopy (PCM) may be performed to quantify adsorbed moisture on the interacting surfaces to validate the hypothesized basis for the RH effects. FIG. 6 shows PCM studies of the changing levels of adsorbed moisture on stainless steel and PERSPEX® at varying RH levels. The dark coloration, which is an indication of the presence of adsorbed molecular water on the two surfaces, increases with increasing RH on the hydrophilic steel but is essentially constant on the hydrophobic Perspex®. FIG. 7 shows measured adhesion forces between a silicon nitride cantilever probe and the two surfaces, with the top of FIG. 7 showing PCM portraits of stainless steel at varying RH, and the bottom of FIG. 7 showing measured adhesion force between a silicon nitride cantilever and a stainless steel and a Perspex® substrate). Referring to FIG. 7, the RH has a substantial effect on the adhesion to the hydrophilic surface, but a negligible effect on the adhesion to the hydrophobic surface.

When explosives compounds are placed under tensile stress (e.g., during swab-based removal) or compressive stress (e.g., during swab-based removal and under adhesive load during residue deposition), they will deform and possibly yield as a function of their mechanical properties. Solid crystalline materials (e.g., TNT) are relatively easy to describe, as they generally will not yield except under large loads compared to those found during adhesion and swabbing. However, materials such as ANFO, C4, and Semtex will deform significantly during adhesion and removal. The following description focuses on the deformation during removal aspect, as it is most closely linked to the effectiveness of the swabbing process.

The approach employed in this example to characterize the deformation and failure of the explosives compound during swabbing may be traced back to the process of attrition and breakage during granulation used in powder processing industries, such as the food and pharmaceutical industries. Failure modes during attrition are plastic and brittle. When plastic failure occurs, the material may deform with no major crack and no peak stress from a stress-strain analysis. The material may be described as flowing like a paste or smearing. Brittle failure occurs after a major crack forms; a peak flow stress will clearly be present. In either scenario, the deformation or failure is not recoverable. These are the mechanisms by which an explosive compound (C4, Semtex) will fail when it is swabbed from a surface. Depending on the failure mechanism, the optimal swabbing technique will change. In the present example, ANFO and TNT are removed as discrete particles, and as such their mechanical properties are not expected to be as important to swabbing effectiveness.

Granule failure may be described based on the properties of the particles and binder material in the composite, as shown by Equation 6. Here, $\sigma_p$ is defined as the peak flow stress; $d_{32}$ is the specific surface mean particle size (or Sauter mean); $\gamma$ is the binder surface energy; $\theta$ is the solid-liquid contact angle; $\mu$ is the binder viscosity; and $\dot{\varepsilon}_a$ represents the strain rate. $\mu_f$ is the coefficient of internal friction; S is the granule liquid saturation; and $\Phi$ is the granule packing fraction. Particle shape is not considered here.

$$\frac{\sigma_p d_{32}}{\gamma \cos \theta} = f\left(\frac{\mu \dot{\varepsilon}_a d_{32}}{\gamma \cos \theta}, \mu_f, S, \phi\right) \quad (6)$$

The left side of Equation 7 is called the dimensionless peak flow stress, Str*, which represents the dynamic strength normalized against capillary forces. The first term on the right side of Equation 7 is called the capillary number (Ca) and is the ratio of viscous to capillary forces. Generally, viscous forces are considered dominant when Ca>1 and negligible when Ca<$10^{-3}$. The remaining terms are often constant within a system of fixed composition. Compression tests, coupled with knowledge of particle and binder properties, allow the analysis of granule breakage to be discussed in terms of Str* and Ca. Generally, if Ca<$10^{-3}$, then the failure is considered brittle. If Ca>$10^{-3}$, failure is considered plastic. A plot of the dimensionless stress as a function of the capillary number for a system will collapse onto a single curve, as shown by Equation 7, where $k_1$, $k_2$ and n are fitted parameters related to the composition and packing of the composite. Families within a system will exhibit the failure curves of the same general shape, with the transition region occurring at approximately identical values of the capillary number.

$$Str^* = k_1 + k_2 Ca^n \quad (7)$$

Pellets of simulated C4 and Semtex are prepared to have mechanical and compositional properties representative of active compounds. Two major contributors determining plasticity of a composite are strain rate and viscosity. Because the composition of the binder will be held constant for each material, viscosity will be constant. The failure characteristics of the simulated explosives compounds are then studied as a function of strain rate and applied load. When creating the simulated C4 and Semtex 1A, the particle size distribution, mean particle size, density, and binder viscosity are matched to active explosive compounds. The subsequent stress-strain test is performed using a dynamic and static fatigue testing device such as an Instron Electro-Puls E1000 Electrodynamic Test Instrument. When the composite fails at high strain, this is considered plastic deformation. When plastic deformation occurs, a clear maximum may not exist on the stress-strain plot generated by compression experiments. Conversely, a clear maximum exists on the stress-strain curve when the material fails in a brittle fashion.

In the present example, the modes of adhesive failure between the different explosives and the 11 substrates and the swabs fabricated are obtained as a function of RH. For the TNT and ANFO, these results are in the form of descriptions of whether individual particles or prills break free from the substrate and adhere to the swabs, or whether they do not. For the C4 and Semtex 1A, the relationship between the load applied during the swabbing, the swab- and substrate-residue interaction forces, and the mode of failure of the residue (either within the body of the residue or at the residue-substrate or residue-swab interface) is determined. This information guides the development of the swabs, by indicating whether more or less contact between the swab and residue is necessary, whether the swab needs to surround the residue or simply contact the top of the residue, and whether the swab-residue adhesion force is adequate or must be increased.

Both nano-patterned and micro-patterned macromolecular swabs may be fabricated and tested with controlled chemical, mechanical, and electrical properties for use in swab-based sampling. These swabs are designed with a focus on: interrogating features on the substrate of interest effectively; resisting the accumulation of static charge during swabbing and sample desorption in the ion mobility spectrometry (IMS); adhering to the explosives residues with sufficient force to extract them from topography on the substrate while retaining the ability to release the residues in the thermal desorber of the IMS; and ensuring mechanical, chemical and thermal stability of the swabs during use so that the swabs have a long operational lifetime and do not become a source of false signals in the IMS.

Figure 8A:
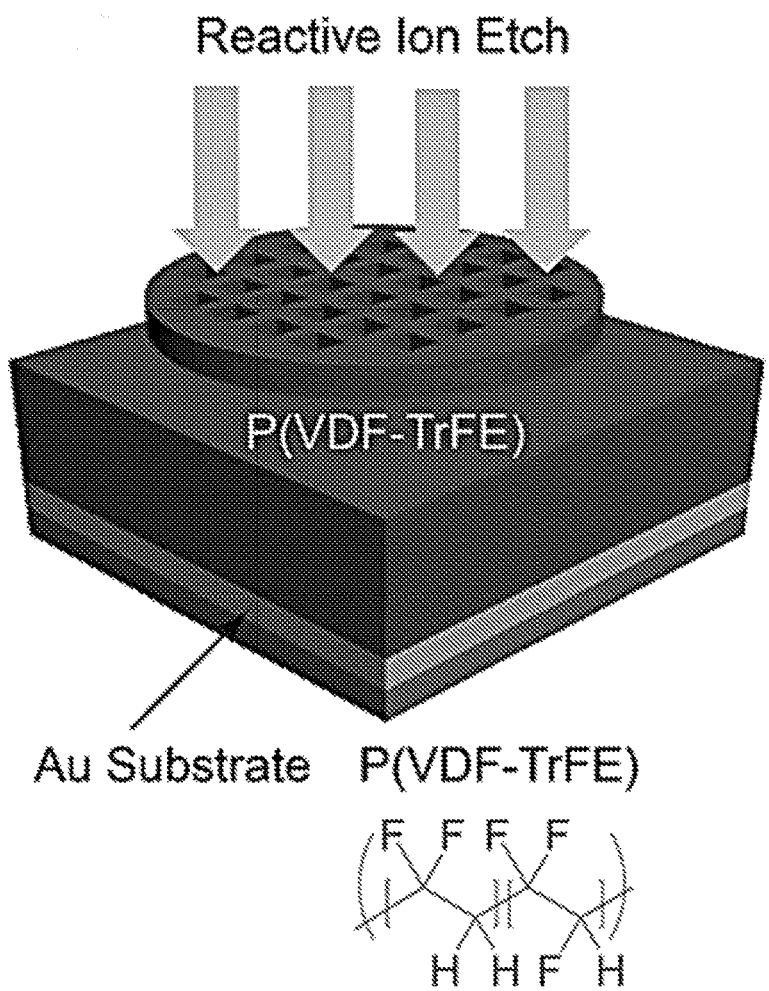
FIG. 8a is a schematic illustration demonstrating how a simple material such as a copper grid may serve as a mask for the high throughput fabrication of the swabs, with an inset showing the chemical structure of the sacrificial polymer P(VDF-TrFE).

As a further example, two sacrificial templating routes are utilized in order to generate a microstructured conducting polymer layer. In either instance, the general strategy for the formation of the freestanding, microtextured film is illustrated in FIG. 8a (which shows a schematic illustration demonstrating how a simple material such as a copper grid may serve as a mask for the high-throughput fabrication of the swabs, with an inset showing the chemical structure of the sacrificial polymer P(VDF-TrFE)) and FIG. 8b (showing an AFM image of the P(VDF-TrFE) active layer after patterning with the reactive ion etch (RIE) process; the darker regions represent the gold substrate while the lighter regions represent the remaining polymer template)). The first methodology uses simple lithographic techniques to create micropatterened brushes (dimensions between 1-100 μm). This scalable methodology is of prime import in transitioning from the laboratory to device scale-up. In a second methodology, commercially-available anodized aluminum oxide (AAO) membranes are used to generate patterns on the 0.2-1 μm. By having these two different, yet mass-producible, templating methodologies, structured swabs may be created with feature scales spanning four orders of magnitude while still keeping technology transfer at the fore.

Figure 8B:
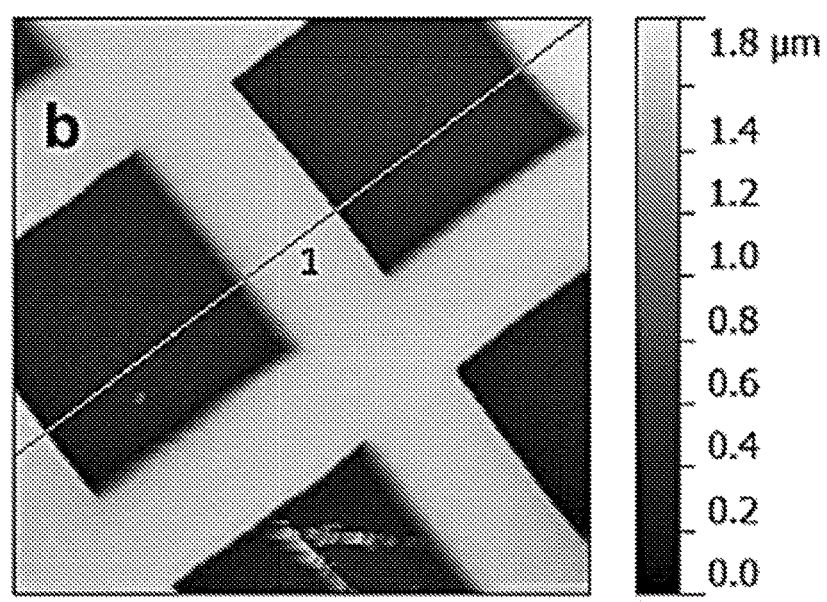
FIG. 8b is an AFM image of the P(VDF-TrFe) active layer after patterning with the reactive ion etch (RIE) process.

As a demonstrative example, a copper grid is utilized as a mask to remove parts of a templating polymer film selectively. A RIE procedure, which does not require solvents or liquid chemical etchants, is utilized to ablate the sacrificial polymer film, and a copper grid is used to mask the portions of the polymer film that are to be left after templating (FIG. 8a). The sacrificial polymer (whose chemical structure is inset into FIG. 8a) used currently is poly (vinylidenefluoride-co-trifluoroethylene) [P(VDF-TrFE)] as it has high thermal and chemical stability for the etching and electrochemical polymerization procedures. Furthermore, it is a commercial polymer that can be obtained inexpensively in large quantities. As shown in FIG. 8b, this process yields microporous thin films with regularly-patterned square holes on the order of 80 μm and with supporting spacer layers of 40 μm. It is noted that the texture of the pattern can be changed across the film by applying different masks to different sections of the continuous polymer film. In this example, the supporting substrate is a gold electrode from which a conducting polymer can be polymerized readily. Similar patterns are generated by using an AAO template in place of the copper grid, and using the same substrate, sacrificial polymer, and RIE procedure (images not shown). By utilizing the AAO templates, the sizes and spacings of the microporous structure are able to be tuned in a straightforward manner.

Figure 9A:
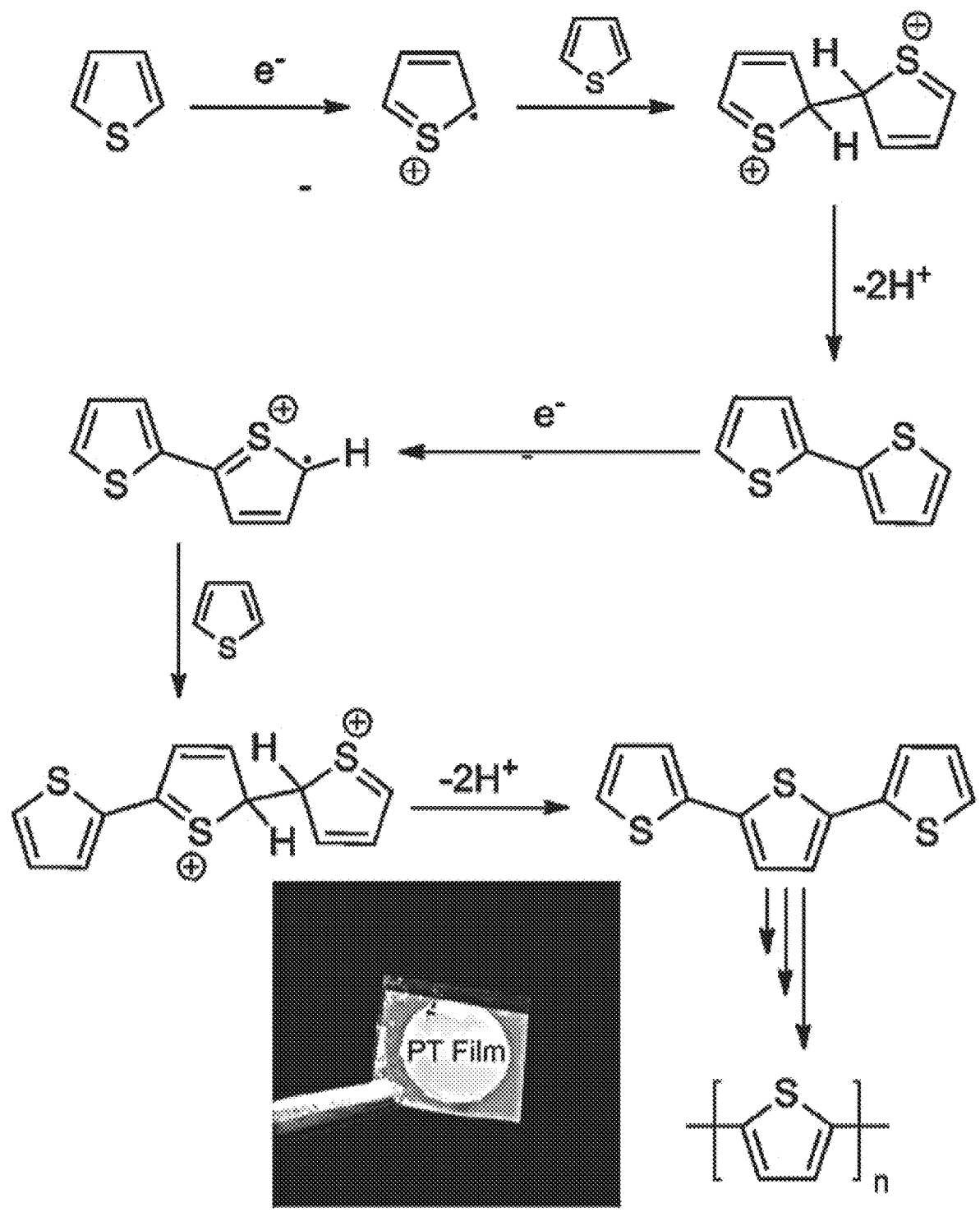
FIG. 9a is an image showing the reaction mechanism of electropolymerization of substituted and unsubstituted polythiophenes in bulk solutions.

After patterning of the sacrificial polymer template, a conducting, thermally-stable macromolecule is able to be polymerized into the residual pores through electrochemical methods by taking advantage of the exposure of the gold substrate. In initial studies we have begun working with polythiophene (PT) as the model conducting polymer. This material was chosen due to its relatively high degradation temperature (Td>300° C.), high chemical resistance, and relatively high charge conductivity for a polymer species ($\sigma \sim 10^{-3}$ S cm$^{-1}$). It is also of note that polythiophene degrades prior to melting. As such, any pillars of PT will not collapse during exposure to elevated temperatures. Polymerization of conducting and semiconducting polymers by application of an applied bias is a well-established technique. In fact, the electropolymerization of substituted and unsubstituted polythiophenes in bulk solutions has been studied in detail and the reaction is found to proceed via a mechanism that includes a radical cation intermediate (FIG. 9a). In turn, a number of solvents and supporting electrolytes have been examined in order to optimize the thiophene electropolymerization reaction. In this manner, achievement of the polymerization kinetics in planar and confined geometries is straightforward to establish and is critical in the scale-up of the herein disclosed procedure.

Figure 9B:
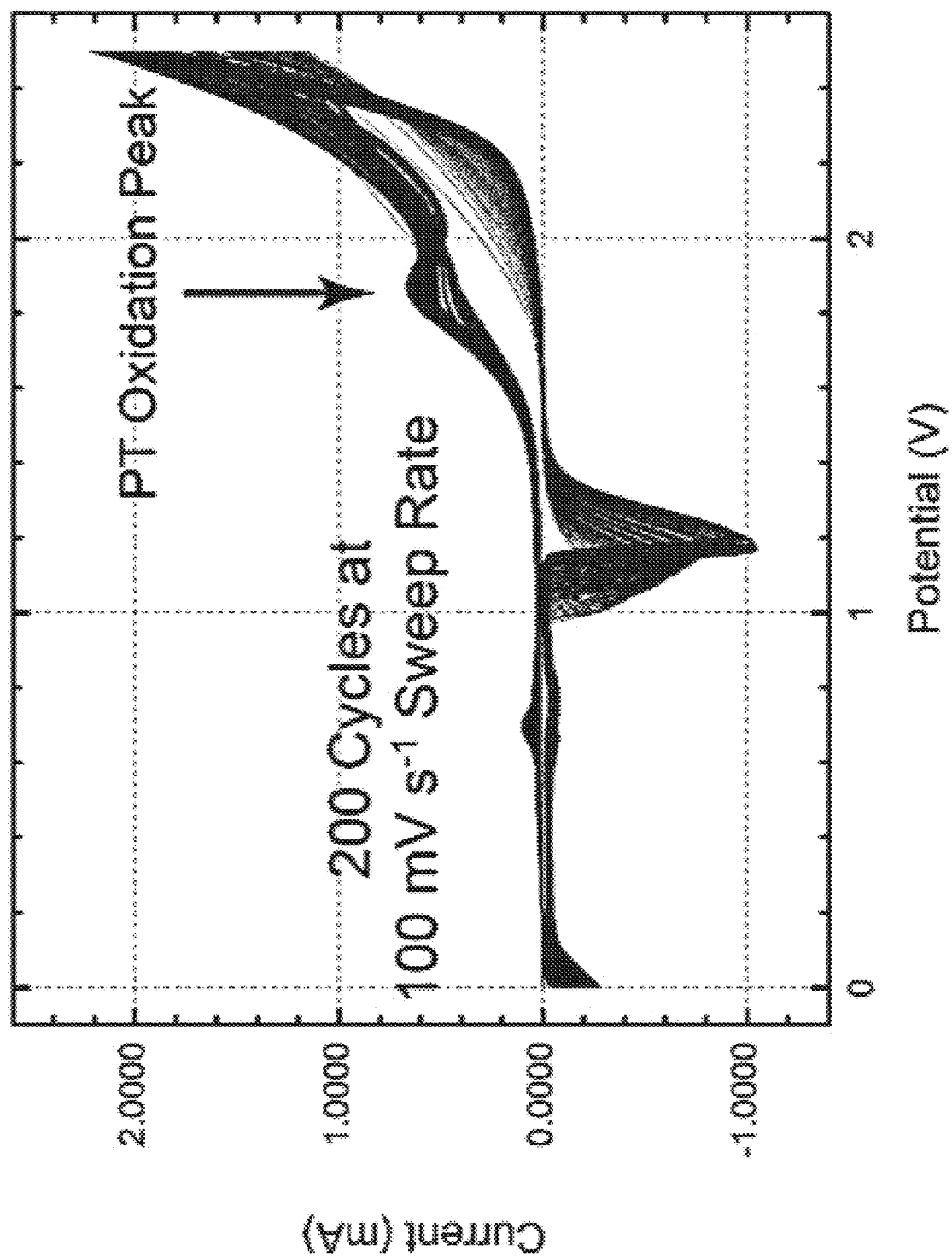
FIG. 9b is a cyclic voltammogram (CV) trace for the deposition of thiophene on the working electrode versus an Ag/AgCl reference electrode.

The above example demonstrating initial electrochemical polymerization results demonstrates the ability to coat metallic substrates with polythiophene in a straightforward manner (see inset of FIG. 9b; FIG. 9b is a cyclic voltammogram (CV) trace for the deposition of thiophene on the working electrode versus an Ag/AgCl reference electrode)). The CV peak at V=1.8 V (against a silver/silver chloride reference electrode) was associated with the electron transfer that corresponded to the addition of a repeat unit of thiophene to the working electrode with an active area of 0.79 cm$^2$. Here, 12.5 mM thiophene was polymerized from a dichloromethane (a non-solvent for the ferroelectric polymer) solution containing 0.1 M tetrabuytylamomonium perfluoroborate as a supporting electrolyte for 200 cycles with a sweep rate of 100 mV s$^{-1}$ (FIG. 9b). Therefore, growing a multiple micron-thick film required just slightly over an hour of deposition time. This is in-line with electrochemical deposition timescales used currently in commercial practice. A picture of the PT thin film is shown in the inset of FIG. 9b. Here, the polythiophene appears as a circular pattern on the gold electrode due to the experimental deposition system used. This observable visible change feature allows for the rapid, on-line screening of materials in a large-scale fabrication line.

The sacrificial polymer mask must be removed successfully in order to generate the freestanding nanowire film. Identification and quantification of forces on the microscale may be required. Importantly, the template must be removed without the collapse of the conducting polymer wires (i.e., the structure associated with the polymer mask must be maintained when the polymer wires are without support). As such, the domain spacings, domain geometries, and aspect ratio of the polymer wires are of great import. The structural integrity of the polymer wires must be greater than the capillary forces that will arise due to the introduction of solvent to remove the polymer template and the drying of the resultant freestanding wires. While it is anticipated that this will require systematic engineering of the mask removal solvents and processing conditions, this can be achieved in a straightforward manner, as has been done in many examples from the literature.

In order to visualize and characterize the structure of these materials properly, atomic force and electron microscopy (AFM and EM) and grazing-incidence x-ray scattering play a role in the analyses. For instance, one critical structural aspect of the polythiophene nanowires is whether or not they have a preferred crystalline texture on the nanometer length scale due to the confined growth direction. This should increase charge conductivity, and this aids in the ability of the microstructured brush to prevent static charging. In fact, previous studies suggest that a preferred crystalline texture will be present and aid in charge transport out of the device. Additionally, the size, shape, and registry of the spacing of the polythiophene posts across the macroscopic film is of key interest in correlating microstructure with polymer performance.

Figure 10A:
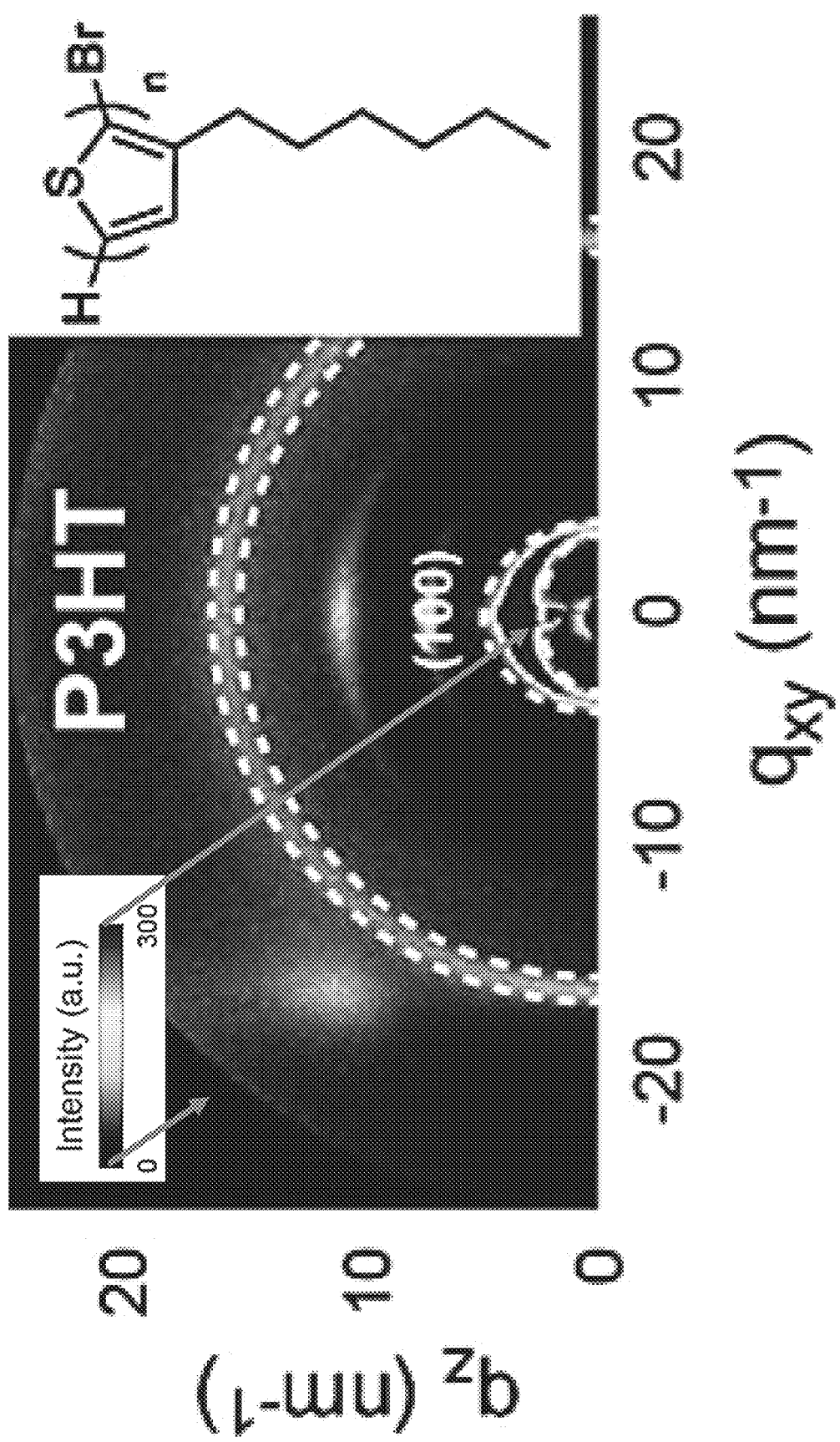
FIG. 10a is an image depicting the grazing-incidence wide-angle x-ray scattering (GI-WAXS) pattern for a poly(3-hexylthiophene) (P3HT) thin film lacking a large degree of crystalline texture.
Figure 10B:
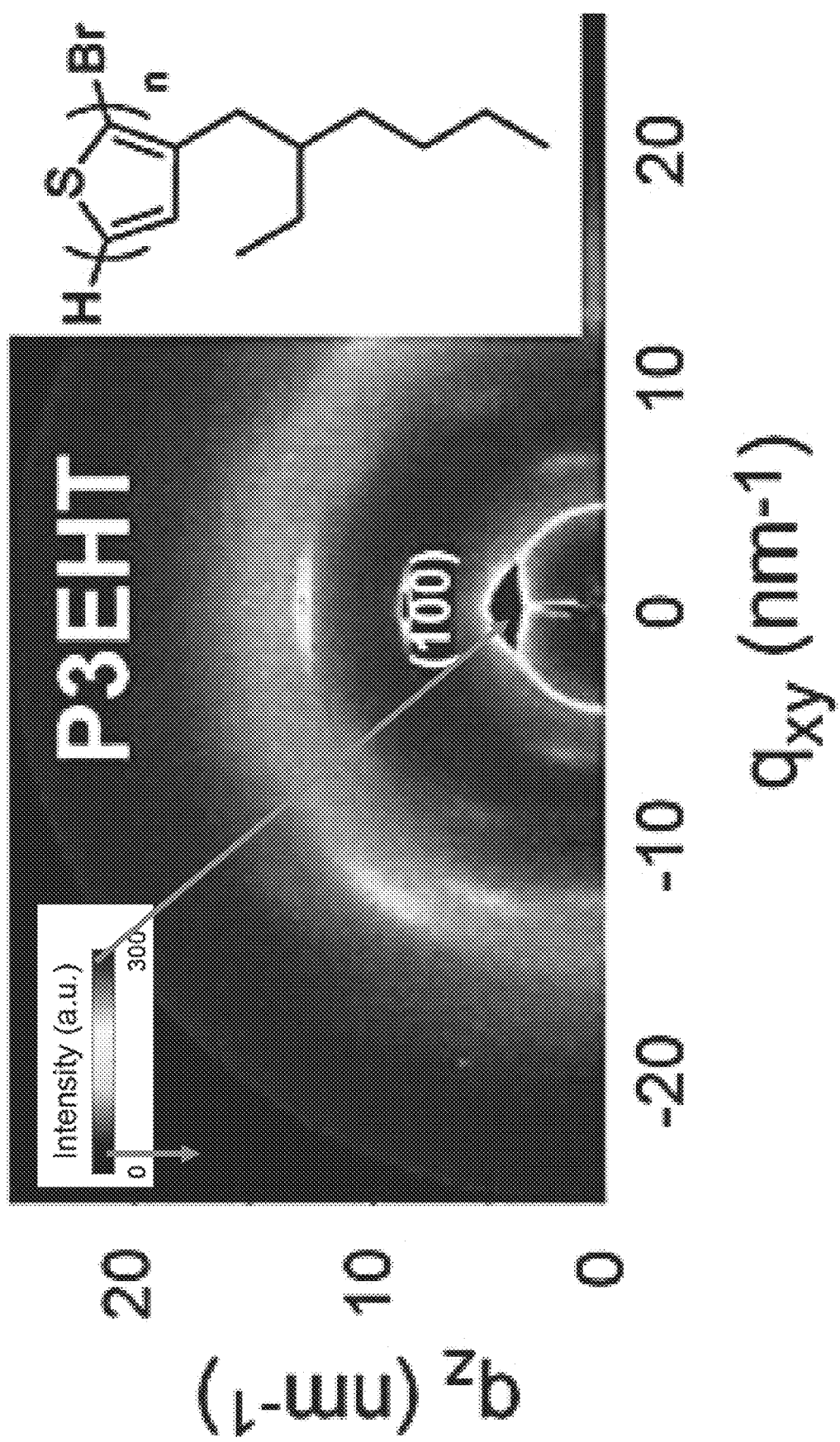
FIG. 10b an image depicting the GI-WAXS pattern for a poly(3-(2'-ethyl)-hexylthiophene) (P3EHT) thin film.

Simultaneous grazing-incidence wide-angle x-ray scattering and small-angle x-ray scattering (GI-WAXS and GI-SAXS) allow determination of these system descriptors. It has been demonstrated that the crystalline texture of poly (3-alklythiophene) thin films can be greatly altered through the side chain substitution of the polymer. FIG. 10a depicts the GI-WAXS scattering pattern for a poly(3-hexylthiophene) (P3HT) thin film lacking a large degree of crystalline texture (i.e., the Bragg reflections appear as halos due to the superposition of many different crystal orientations). On the other hand, the addition of a slight branch in the alkyl chain to generate poly(3-(2'-ethyl)-hexylthiophene) (P3EHT) results in a thin film with discrete reflections (FIG. 10b) even though the two thin films were prepared in the same manner. And, in fact, the relative degree of crystallite orientation can be calculated readily. The combination of GI-WAXS, GI-SAXS, and electron microscopy will allow for the unambiguous determination of the 0.5-5,000 nm morphology of the active layer of the brush. This knowledge is crucial in advancing the physics associated with particle adhesion to the textured substrates.

The degradation and melting temperatures (if any) of the polythiophene wires need to be ensured to be above the required operating ranges for explosive residue detection. A combination of thermogravimetric analysis (TGA) and differential scanning calorimetry (DSC) is utilized to identify any thermal transitions for the bulk polymer and for the microstructured wires. Change in the thermal properties of these materials upon creating the polythiophene wires is not anticipated, but nevertheless it is important to confirm this as maintaining the structural integrity of the brush over multiple (>100 uses) is important.

Additionally, the electrical conductivity of the brush wires is quantified in order to ensure the conductivity of the microstructured domains is equal to or greater than the conductivity of the solid thin film. In this example, conducting probe atomic force microscopy (CP-AFM) is implemented. In this type of geometry the gold substrate serves as one electrode while an electrically-conducting AFM tip serves as the other electrode. The CP-AFM tip approaches the polymer wires gently in order to minimize disruption to the microstructure imparted by the templating and growth procedure. After proper contact is made by the probe tip to the top of the polymer wires, a small voltage can be applied and the current response can be monitored; this allows for the straightforward measurement of the electrical conductivity of the polymer wires. Measurements of the polymer conductivity ensure these materials will be charge dissipative and, as such, the probes will not be subject to static charge effects. This approach allows a quantification of the successes and failures of each generation of a swab, and further allows guided design of an optimized swab.

Figure 11B:
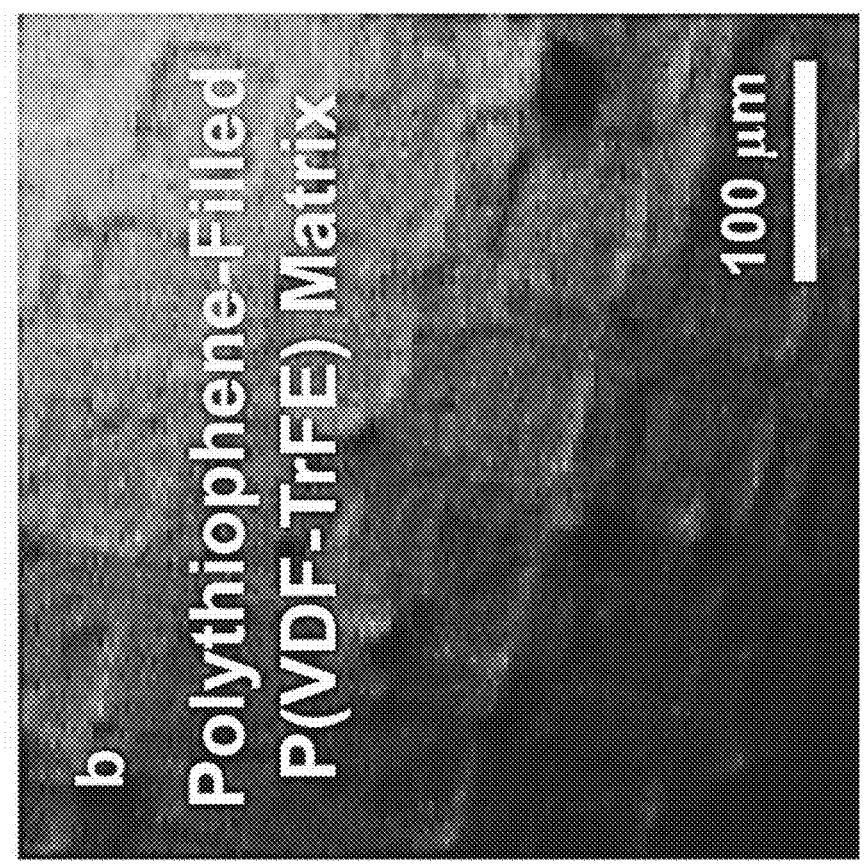
FIG. 11b is an optical micrograph of the same film in FIG. 11a after polythiophene deposition.
Figure 11A:
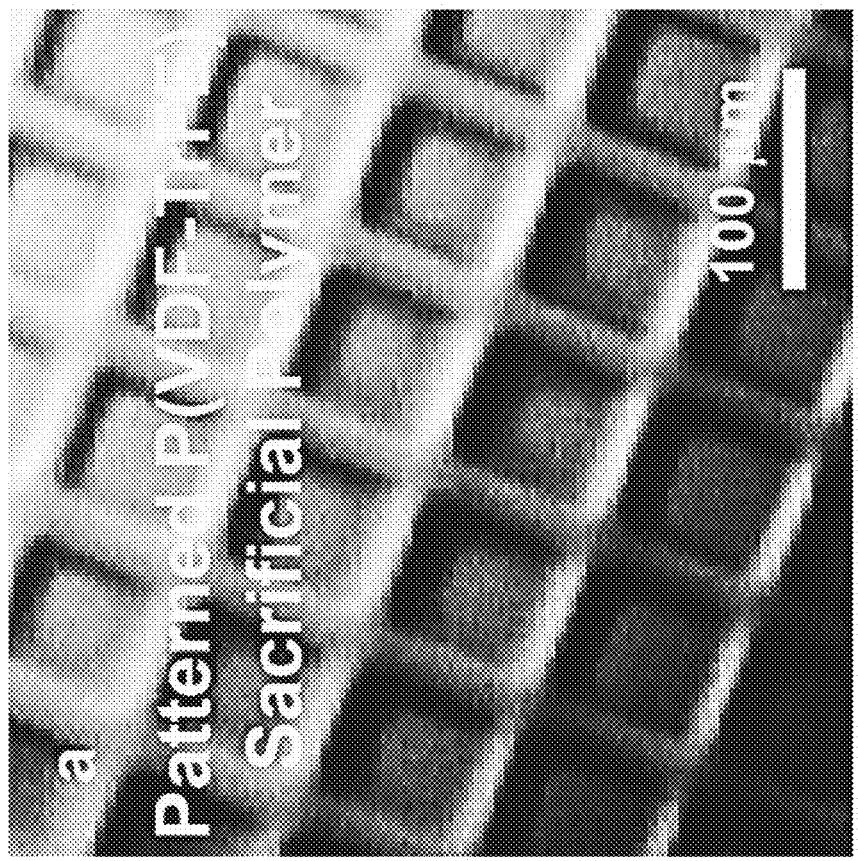
FIG. 11a is an optical micrograph of the patterned P(VDF-TrFE) shown in FIG. 2b prior to polythiophene deposition.

In another embodiment, optimizing the reaction conditions for the electropolymerization of polythiophene is done in confined regions. In particular, the aim is to decipher how the rates of reaction are dependent on the relatively confined geometries associated with the templated sacrificial polymers, as those shown in FIG. 8b. By controlling the electrochemical bath composition, reaction sweep rate, and electrochemical deposition times, the deposition of the polythiophene moiety (and any other conducting polymers deemed fit) is optimized in a straightforward manner. In fact, an initial reported result demonstrates the ability to fill the microporous sacrificial polymer matrix of FIG. 8b with polythiophene (FIGS. 11a and 11b). FIG. 11a is an optical micrograph of the patterned P(VDF-TrFE) shown in FIG. 2b prior to polythiophene deposition. FIG. 11b shows an optical micrograph of the same film after polythiophene deposition, indicating the polythiophene has grown in the pores of the sacrificial polymer and has overgrown the template, an issue that may be avoided by decreasing the deposition time. This demonstrates optimization of the deposition conditions for a variety of geometries and domain spacings such that rapid prototypes may be generated.

Those skilled in the art will recognize that numerous modifications can be made to the specific implementations described above. The implementations should not be limited to the particular limitations described. Other implementations may be possible.

The invention claimed is:

1. A polymeric swab comprising:
a substrate, wherein the substrate comprises a first surface, wherein the first surface comprises copper or gold; and
a plurality of microfabricated fibers over the first surface, wherein the plurality of microfabricated fibers is configured to contain a surface texture that allows for independent motion between microscale regions, wherein a spacing between each microfabricated fibers of the plurality of microfabricated fibers ranges from 10 nm to 100 nm, wherein each microfabricated fiber of the plurality of microfabricated fibers comprises a polymer, wherein the polymer is configured to not outgas at ion-mobility spectrometry conditions.

2. The polymeric swab of claim 1, the plurality of microfabricated fibers are optimally configured to interrogate surfaces.

3. The polymeric swab of claim 1, the plurality of microfabricated fibers having characteristic heights and diameters.

4. The polymeric swab of claim 1, the plurality of microfabricated fibers are reusable.

5. The polymeric swab of claim 1, the plurality of microfabricated fibers are fabricated from optoelectronically-active elements to minimize static charging during repeated use.

6. The polymeric swab of claim 1, the plurality of microfabricated fibers are thermally stable.

7. The polymeric swab of claim 1, further comprising the plurality of microfabricated fibers being polythiopene based polymers.

8. The polymeric swab of claim 1, further comprising heights and diameters ranging from about 1 to about 25 μm.

9. The polymeric swab of claim 1, further comprising the ability to withstand temperatures between about 200° C. to about 350° C.

10. The polymeric swab of claim 1, wherein an adhesion of the plurality of microfabricated fibers and the first surface is based on at least one of mechanical adhesion, electrical adhesion, or chemical adhesion.

11. A swab comprising:
a substrate, wherein the substrate comprises a first surface, wherein the first surface comprises copper or gold; and
a plurality of microfabricated fibers over the first surface, wherein a spacing between each microfabricated fibers of the plurality of microfabricated fibers ranges from 10 microns to 200 microns, wherein the each microfabricated fibers of the plurality of microfabricated fibers comprises polythiopene.

12. The polymeric swab of claim 11, wherein each microfabricated fiber of the plurality of microfabricated fibers comprises a height ranging from about 1 micrometer to 25 micrometers.

13. The polymeric swab of claim 11, wherein each microfabricated fiber of the plurality of microfabricated fibers comprises a diameter ranging from about 1 micrometer to 25 micrometers.

* * * * *